United States Patent [19]

Paganelli

[11] Plant 4,639

[45] Feb. 3, 1981

[54] NECTARINE TREE

[76] Inventor: Frank Paganelli, Rte. #2 Box 2317-A, Wapato, Wash. 98951

[21] Appl. No.: 14,134

[22] Filed: Dec. 17, 1979

[51] Int. Cl.[3] ..... A01H 5/03

[52] U.S. Cl. ..... Plt./41

[58] Field of Search ..... Plt./41

*Primary Examiner*—Robert E. Bagwill

*Attorney, Agent, or Firm*—Christensen, O'Connor, Johnson & Kindness

[57] ABSTRACT

An improved nectarine tree originating as a bud mutation of Stark "Red Gold". This new variety produces freestone fruit the skin of which is a full deep red when fully ripe and which is mottled with yellow in the ripening stages, full ripeness occurring some two to three days earlier than the fruit of the parent variety.

1 Drawing Figure

BACKGROUND

This invention or discovery relates to a new and distinct variety of nectarine tree which bears yellow-fleshed freestone fruit having a deep red skin color when fully ripe and which is mottled with yellow during the ripening stages. This new variety is of the type embraced by group III of the classification of Callavet and Souty, Monographic des Principals Varietes de Pechers, 1950 edition, page 46. This new variety originated as a bud mutation of Stark "Red Gold" in the applicant's orchard located near Wapato, Wash. and has been asexually reproduced at said location by topworking of mature orchard trees so as to establish the genetic stability of the new variety through successive generations.

As compared with Sun Grand (U.S. Plant Pat. No. 974) has leaves with reniform instead of globose glands and bears fruit which is larger in size, ripens approximately ten days earlier and has less red exterior color during the ripening stages. It ripens some two to three days earlier than its parent "Red Gold" which it otherwise resembles in most respects other than the deeper red and more uniform red color of the fruit at full ripeness of the new variety as compared with the parent variety.

DRAWING

The photographic print depicts a branch of the new variety with fruit approaching full ripeness.

DETAILED DESCRIPTION

Leaves of the new variety tend to be slightly lighter in color than those of "Red Gold" and slightly more folded in form.

The following outline of characteristics applies to the new variety, the major color plate identifications being reference to Maerz and Paul Dictionary of Color, except where common terms of color definition are employed.

Tree:
- *Size.*—Large to medium.
- *Vigor.*—Vigorous.
- *Production.*—Productive.
- *Bearing.*—Regular bearer.

Leaves:
- *Size.*—Stocky to medium.

- *Thickness.*—Thick to medium.
- *Margin.*—Glandular; crenate.
- *Petiole.*—Medium length; medium thickness.
- *Glands.*—Large to medium; reinform. Position — usually two on petiole and two or more on blade.

Color:
- *Top size.*—Medium green (22-L-6 to 22-L-8).
- *Undersize.*—Lighter green (21-K-6).

Flowers: Blooming period (1978).
- *Date of first bloom.*—April 7.
- *Date of full bloom.*—April 15. Medium as compared with other varieties.
- *Size.*—Large.
- *Type.*—Showy.

Fruit:
- *Maturity when described.*—Eating ripe — Aug. 15, 1978.
- *Date of first picking.*—Aug. 10, 1978.
- *Date of last picking.*—Aug. 14, 1978.

Size: Variable.
- *Average diameter axially.*—2⅝".
- *Average transversely in suture plane.*—2 -7/16".

Form: Variable; symmetrical; globose to oblong.

Suture: Distinct; extends from base to apex, with slight depression beyond pistil point.

Cavity: Rounded, deep.

Base: Rounded.

Apex: Short.

Skin:
- *Thickness.*—Thick to medium.
- *Texture.*—Medium.
- *Tendency to crack.*—None noted.
- *Color.*—Red (5-1-12) when ripe and during ripening the red being mottled with yellow (10-L-3) shading to orange-yellow (9-k 8 to 10-L-12).

Flesh:
- *Texture.*—Medium; crisp; melting.
- *Ripens.*—Even.
- *Flavor.*—Subacid; delicate.
- *Eating quality.*—Good. Excellent when fully mature.
- *Color.*—Yellow (9-1-2 shading to 9-J-5), with considerable red (3-L-3) adjacent to stone; the surface of the pit cavity being red with yellow fibers.

Stone:
- *Type.*—Free.
- *Size.*—Medium.

*Form.*—Oblong.
*Apex.*—Acute.
*Sides.*—Equal.
*Ridges.*—Jagged.
*Pits.*—Elongated.
*Ventral edge.*—Thin.
*Dorsal edge.*—Full.
*Tendency to split.*—Slight.
*Color.*—Brown (5-A-12).

Use: Market.

*Keeping quality.*—Good.
*Shipping quality.*—Good.

The tree and its fruit herein described may vary in slight detail due to climatic and soil conditions under which the variety may be grown, the present description applying to the variety as grown in the lower Yakima Valley of Washington.

I claim:

1. A new and distinct variety of nectarine tree similar to its parent Stark "Red Gold" except for the darker redder color of the fruit skin and the slightly earlier maturation of the fruit, together with the tendency for the leaves to be slightly lighter in color than those of the parent and slightly more folded in form as shown and described.

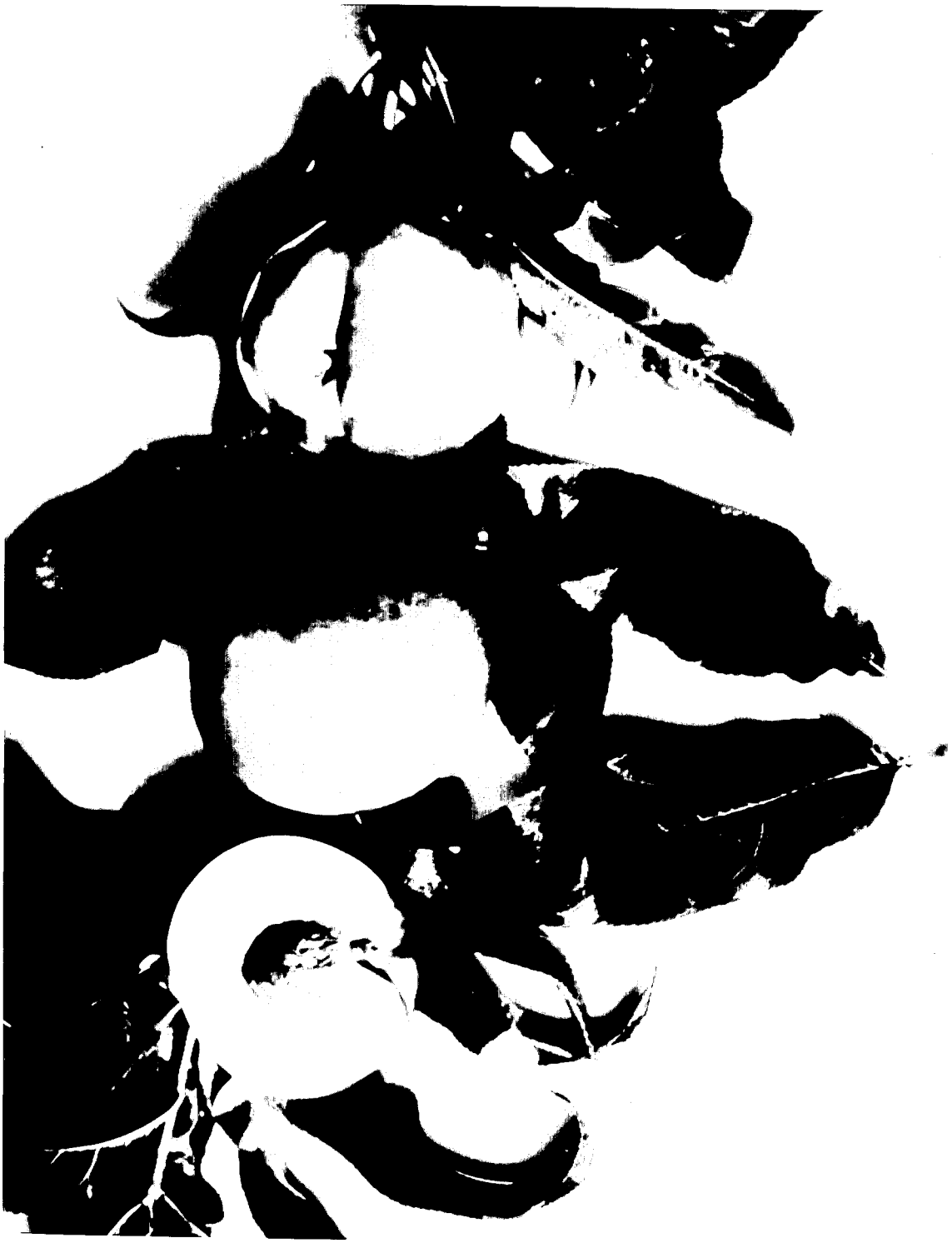

* * * * *